United States Patent [19]
Mohnot et al.

[11] Patent Number: 5,747,003
[45] Date of Patent: May 5, 1998

[54] AMORPHOUS PRECIPITATED SILICA ABRASIVE

[75] Inventors: Shantilal M. Mohnot, Murrysville; Harold E. Swift, Gibsonia; Thomas G. Krivak, Irwin; Robert H. Fear, Pittsburgh; Laura M. Randall, Pittsburgh; Laurence E. Jones, Pittsburgh, all of Pa.

[73] Assignee: PPG Industries, Inc., Pittsburgh, Pa.

[21] Appl. No.: 408,327

[22] Filed: Mar. 22, 1995

[51] Int. Cl.$^6$ .............................. A61K 7/16; B01J 23/00; C01B 33/12

[52] U.S. Cl. ........................ 424/49; 423/335; 423/338; 423/339; 106/481; 106/482; 106/492; 501/133; 502/407; 502/233; 502/232

[58] Field of Search ....................... 423/335, 339, 423/324, 338; 106/481, 482, 492; 502/407, 233, 232; 501/133; 424/49

[56] References Cited

U.S. PATENT DOCUMENTS

| | | | |
|---|---|---|---|
| 4,420,312 | 12/1983 | Wason | 51/308 |
| 4,463,108 | 7/1984 | Wagner et al. | 523/216 |
| 4,992,251 | 2/1991 | Aldcroft et al. | 423/335 |
| 5,110,336 | 5/1992 | Kadunce et al. | 65/24 |
| 5,114,438 | 5/1992 | Leatherman et al. | 51/296 |

FOREIGN PATENT DOCUMENTS

B-65777/86  6/1987  Australia.

OTHER PUBLICATIONS

ASTM Designation: C 690–86, "Standard Test Method for Particle Size Distribution of Alumina or Quartz by Electric Sensing Zone Technique", pp. 217–220 (No date).

ASTM Designation: C 819–77, "Standard Test Method for Specific Surface Area of Carbon or Graphite" (No Date).

ASTM Designation: D 2414–93, "Standard Test Method for Carbon Black—n–Dibutyl Phthalate Absorption Number[1]", pp. 451–455 (No date).

F. E. Albus, "the Modern Fluid Energy Mill", Chemical Engineering Progress, vol. 60, No. 6, Jun., 1964, pp. 102–106.

J. H. Perry, Chemical Engineers Handbook, 4th Ed., McGraw–Hill Book Co., 1963, pp. 8-42–8-43.

W. L. McCabe et al, Unit Operations of Chemical Engineering, 3rd Ed., McGraw–Hill Book Co., 1976, pp. 844–845.

R. J. Grabenstetter et al, "The Measurement of the Abrasion of Human Teeth by Dentifrice Abrasives: A Test Utilizing Radioactive Teeth", J Dent Res 37: 1060–1068, 1958.

J. J. Hefferren, "A Laboratory Method for Assessment of Dentifrice Abrasivity", J Dent Res, Jul.–Aug. 1976, pp. 563–573.

Primary Examiner—James J. Seidleck
Assistant Examiner—Michael A. Williamson
Attorney, Agent, or Firm—George D. Morris

[57] ABSTRACT

A statistically large population of particles of amorphous precipitated silica comprising pigmentary phase particles and glassy phase particles and having a glassy phase fraction in the range of from 0.3 to 30 area percent is useful as an abrasive for dentifrice compositions, especially toothpaste.

24 Claims, 2 Drawing Sheets

AMORPHOUS PRECIPITATED SILICA ABRASIVE

BACKGROUND OF THE INVENTION

Dentifrice compositions are well known and well characterized in the literature, including, but not limited to patent specifications. Toothpaste compositions contain a number of specific components for specific purposes. Among the more common components often included in dentifrice compositions are abrasives, fluoride sources, binders, preservatives, humectants, anti-plaque agents, coloring agents, water, and flavoring agents. The foregoing listing is exemplary only, and it is not necessary that all be present. Similarly, other ingredients not included in the listing may be present. Toothpaste is the most common type of dentifrice composition, but dry powders are often used.

The purpose of the abrasive is to provide appropriate cleaning and plaque removal without subjecting the tooth itself to excessive abrasion. Commonly used abrasives include alumina, calcium carbonate and calcium phosphates. More recently synthetic silicas have been used because of their efficient cleaning, compatibility with other ingredients, and physical properties. Among the synthetic silicas that have been used are amorphous precipitated silicas.

There are many different types of amorphous precipitated silicas, some of which are suitable as abrasives for dentifrice compositions and some which are not. Among those which are suitable there are many different kinds which have different properties, different abrasive qualities, and different compatibilities with other ingredients of the dentifrice composition.

SUMMARY OF THE INVENTION

A new class of amorphous precipitated silicas has now been found which is especially effective as abrasive for dentifrice compositions, particularly the toothpastes. Accordingly, a first embodiment of the invention is a statistically large population of particles of amorphous precipitated silica comprising pigmentary phase particles and glassy phase particles and having a glassy phase fraction in the range of from 0.3 to 30 area percent.

BRIEF DESCRIPTION OF THE DRAWINGS

For a better understanding of the invention, reference may be made to the drawings in which.

DETAILED DESCRIPTION OF THE INVENTION

Figure 1:
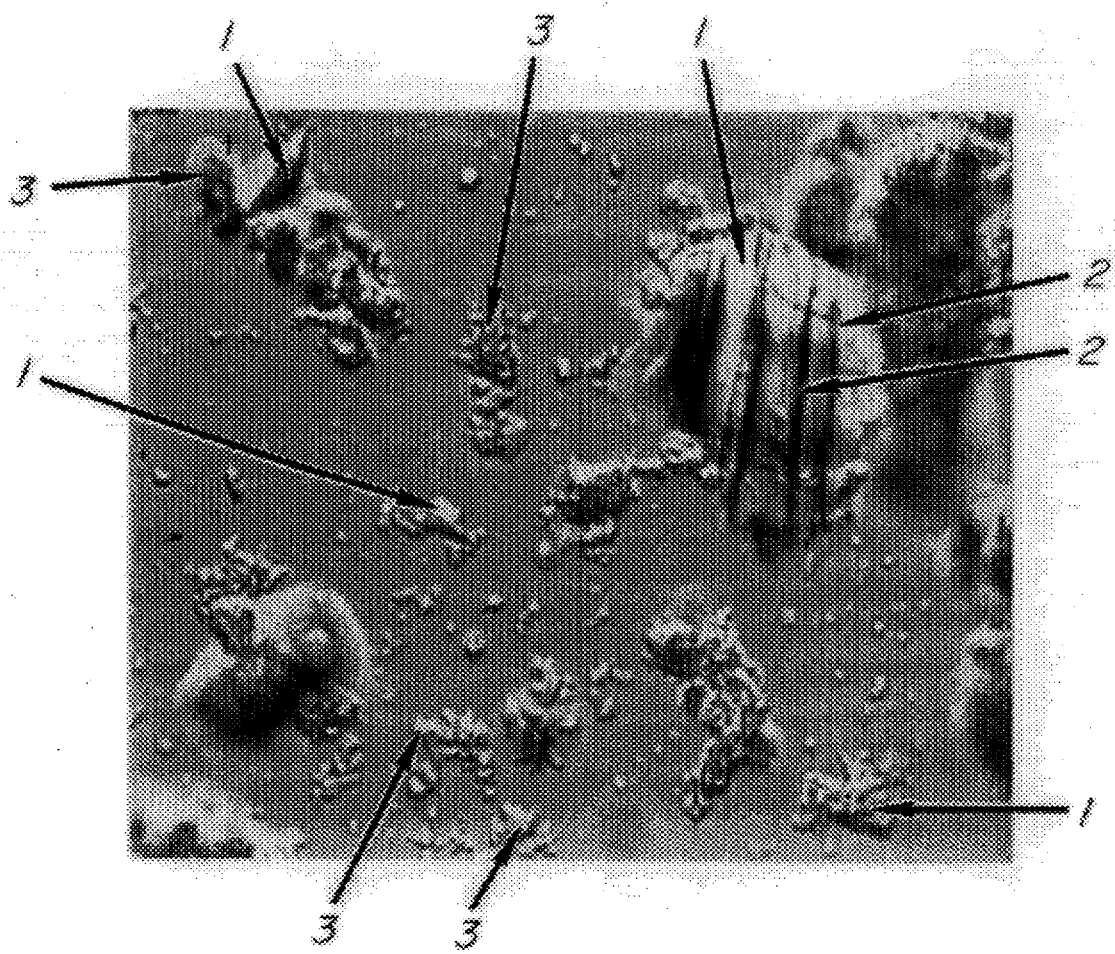
FIGS. 1 and 2 are photomicrographs of amorphous precipitated silica of the invention dispersed, respectively, in different oils.

Although both are silicas, it is important to distinguish amorphous precipitated silica from silica gel inasmuch as these different materials have different properties. Reference in this regard is made to R. K. Iler, *The Chemistry of Silica*, John Wiley & Sons, New York (1979), Library of Congress Catalog No. QD 181.S6144. Note especially pages 15–29, 172–176, 218–233, 364–365, 462–465, 554–564, and 578–579.

Silica gel is usually produced commercially at low pH by acidifying an aqueous solution of a soluble metal silicate, customarily sodium silicate, with acid. The acid employed is generally a strong mineral acid such as sulfuric acid or hydrochloric acid although carbon dioxide is sometimes used. Inasmuch as there is essentially no difference in density between the gel phase and the surrounding liquid phase while the viscosity is low, the gel phase does not settle out, that is to say, it does not precipitate. Silica gel, then, may be described as a non-precipitated, coherent, rigid, three-dimensional network of contiguous particles of colloidal amorphous silica. The state of subdivision ranges from large, solid masses to submicroscopic particles, and the degree of hydration from almost anhydrous silica to soft gelatinous masses containing on the order of 100 parts of water per part of silica by weight, although the highly hydrated forms are only rarely used.

Amorphous precipitated silica is usually produced commercially by combining an aqueous solution of a soluble metal silicate, ordinarily alkali metal silicate such as sodium silicate, and an acid so that colloidal particles will grow in weakly alkaline solution and be coagulated by the alkali metal ions of the resulting soluble alkali metal salt. Various acids may be used, including the mineral acids and/or carbon dioxide. In the absence of a coagulant, silica is not precipitated from solution at any pH. The coagulant used to effect precipitation may be the soluble alkali metal salt produced during formation of the colloidal silica particles, it may be added electrolyte such as a soluble inorganic or organic salt, or it may be a combination of both.

Amorphous precipitated silica, then, may be described as precipitated aggregates of ultimate particles of colloidal amorphous silica that have not at any point existed as macroscopic gel during the preparation. The sizes of the aggregates and the degree of hydration may vary widely.

Amorphous precipitated silica powders differ from silica gels that have been pulverized in ordinarily having a more open structure, that is, a higher specific pore volume. However, the specific surface area of precipitated silica as measured by the Brunauer, Emmett, Teller (BET) method using nitrogen as the adsorbate, is often lower than that of silica gel.

As used herein and in the claims, a "statistically large population of particles of amorphous precipitated silica" means that the number of particles constituting the population of particles is at least large enough that when the population is arbitrarily divided into halves, the glassy phase fraction of the amorphous precipitated silica of one half is substantially the same as that of the other half.

Also as used herein and in the claims, the glassy phase fraction of the statistically large population of particles of amorphous precipitated silica of the invention is determined in accordance with the procedure which follows.

A portion of a sample of the statistically large population of particles of amorphous precipitated silica to be measured is dispersed in an oil having an index of refraction, $n_D^{25}$, of 1.550±0.0002. The dispersion is then observed with an optical microscope at from 100× to 200×. This allows the microscopist a representative overview of the entire silica particle population, to evaluate the uniformity of the silica dispersion, and to assess morphology and particle size characteristics. Usually the pigmentary phase particles are recognizable as smooth surfaced rounded to sub-angular agglomerates of variable size which are ordinarily isotropic in cross-polarized light.

The Becke Line method is used to determine the index of refraction of the non-glassy phase particles (hereinafter "the pigmentary phase particles") of the silica to be measured. The Becke Line method uses refraction of light to initially determine if the pigmentary phase particles have a higher or lower refractive index relative to the particular oil in which the silica is dispersed. From a set of Cargille refractive index immersion oils calibrated at 25° C. at refractive index intervals of 0.002±0.0002 (R. P. Cargille Laboratories, Inc., Cedar Grove, N.J.), a succession of oils having refractive indices progressively closer to refractive index of the pigmentary phase particles of the silica is chosen until no refraction by the pigmentary phase occurs. This is the "matching index immersion oil." When the silica is dispersed in matching index immersion oil, the pigmentary phase particles substantially disappear from view enabling the glassy phase particles to be clearly viewed. Ordinarily the glassy phase particles exhibit varying morphologies ranging from moderately thick tablets which often have ribs and/or wrinkles, to rounded equant nuggets, to thin brittle films.

After the proper matching index immersion oil has been identified, equilibrate and weigh a tin weighing cup having a diameter of 3.2 millimeters and a height of 4 millimeters to obtain its tare weight. A microbalance capable of weighing to six decimal places in grams is employed. Using a microspatula, transfer 0.500±0.015 milligram of the silica to be measured to the tin cup and weigh to two significant figures. Deliver 15 microliters of matching index immersion oil to an optical microslide with an Eppendorf pipette. Invert the tin cup over the oil drop to empty the weighed silica onto the oil drop. Examine the interior of the tin cup at about 25× to ensure that the tin cup is completely empty. If any silica remains, reinvert the cup over the oil drop. If silica still remains in the tin cup, discard the slide and prepare a new sample. After the silica has been deposited on the oil drop, stir the silica into the oil until a substantially uniform distribution is obtained. Place an 18 millimeter diameter No. 1½ cover slip over the slurry and delicately maneuver the cover slip in a rotary motion to further improve the uniformity of the distribution of the silica in the oil. Do not mill or grind the silica. Remove the cover slip holding it horizontally with the slurry side facing downward. Gather the spread-out slurry on the microslide with a razor blade or straight-edged spatula to the smallest area reasonably possible and replace the cover slip on the slurry. This procedure results in a very uniform distribution of silica in the matching index immersion oil.

Examine the silica dispersed in the matching index immersion oil in an optical microscope using differential interference contrast imaging to produce images of the glassy phase particles having good contrast and edge sharpness characteristics.

Randomly select twenty fields at 1000× instrument magnification and capture each digital color image at 1200× using a video recording system. Transfer the image to an image analysis computer, preferably equipped with optical disk storage, and convert the color image to a gray level image. Perform a smoothing function on the gray scale image to eliminate background noise. Threshold the gray image to represent all the glassy phase in a preselected color, usually red, to best match the original image. Using editing tools, manually edit the gray image to match the original image exactly. All the glassy phase particles should now be accurately represented in the selected thresholding color. Transform the gray/red image to a binary image (usually black and white). Establish the scale of the image by drawing a line in the field of view, measuring its length using a ruler, converting the measurement to micrometers using the known magnification, measuring the length of the same line in pixel widths, and calculating the scale of the image in units of pixel widths/micrometer. Calculate the total area of the field. Once determined, the scale of the image and the total area of the field need not be redetermined for other fields unless conditions or procedures have been changed. Ascertain the area of each glassy phase particle by counting the pixels within each such particle and converting the result to square micrometers using the scale of the image. Exclude any particle having an area less than 1 square micrometer. Sum the unexcluded glassy phase areas to obtain the total area glassy phase area for each of the twenty fields. Calculate the fraction of the total field which is occupied by glassy phase, viz., the glassy phase fraction, and express the result as area percent. Average the glassy phase fractions determined for each of the twenty fields to obtain an intermediate glassy phase fraction. For each silica, two samples of the silica are taken and the foregoing procedure is performed twice for each sample. The glassy phase fraction of the silica is taken as the average of the four intermediate glassy phase fractions.

The amorphous precipitated silica of the present invention has a glassy phase fraction in the range of from 0.3 to 30 area percent. Often the amorphous precipitated silica has a glassy phase fraction in the range of from 0.4 to 10 area percent. From 0.5 to 5 area percent is preferred.

The surface area of the statistically large population of particles of amorphous precipitated silica of the present invention may vary widely. In many cases the surface area is in the range of from 30 to 400 square meters per gram. Often the surface area is in the range of from 35 to 300 square meters per gram. From 40 to 200 square meters per gram is preferred. As used in the present specification and claims, the surface area of the statistically large population of particles of amorphous precipitated silica is the surface area determined by the Brunauer, Emmett, Teller (BET) method according to ASTM C 819-77 using nitrogen as the adsorbate but modified by outgassing the system and the sample for one hour at 180° C.

The DBP oil absorption of the statistically large population of particles of amorphous precipitated silica of the present invention may vary widely. Often the DBP oil absorption is from 60 to 200 cubic centimeters per 100 grams ($cm^3/100$ g). Often the DBP oil absorption is from 70 to 175 $cm^3/100$ g. From 75 to 150 $cm^3/100$ g is preferred. As used in the present specification and claims, DBP oil absorption of the amorphous precipitated silica is determined according to ASTM D 2414-93 using dibutyl phthalate as the absorbate.

The amorphous precipitated silica of the present invention is particulate. The particulates may be porous. In most cases the median particle size by volume of the statistically large population of particles of amorphous precipitated silica of the present invention ($D_{50}$) is in the range of from 2 to 50 micrometers (μm). Often the median particle size by volume of the statistically large population of particles of amorphous precipitated silica of the present invention is in the range of from 2 to 20 micrometers. Frequently the median particle size by volume of the statistically large population of particles of amorphous precipitated silica of the present invention is in the range of from 4 to 15 μm. Preferably the median particle size by volume is in the range of from 5 to 13 μm. Sometimes the median particle size by volume is in the range of from 15 to 50 μm. In most instances at least 90 percent by volume of the statistically large population of particles of amorphous precipitated silica of the present invention has particle sizes less than ($D_{10}$) 100 μm. In many cases at least 90 percent by volume of the statistically large population of particles of amorphous precipitated silica of the present invention has particle sizes less than 50 μm. Frequently at least 90 percent by volume of the statistically large population of particles of amorphous precipitated silica of the present invention has particle sizes less than 40 μm. Preferably at least 90 percent by volume of the statistically large population of particles of amorphous precipitated silica of the present invention has particle sizes less than 30 μm. Usually at least 90 percent by volume of the statistically large population of particles of amorphous precipitated silica of the present invention has particle sizes greater than ($D_{90}$) 0.5 μm. Often at least 90 percent by volume of the statistically large population of particles of amorphous precipitated silica of the present invention has particle sizes greater than 1 μm. Preferably at least 90 percent by volume of the statistically large population of particles of amorphous precipitated silica of the present invention has particle sizes greater than 1.5 μm. Sometimes at least 90 percent by volume of the statistically large population of particles of amorphous precipitated silica of the present invention has particle sizes greater than 5 μm. As used herein and in the claims, particle sizes are determined by use of a Coulter® Multisizer II particle size analyzer (Coulter Electronics Limited, Luton, Beds, England) according to ASTM C 690-86 but modified by stirring the filler for 10 minutes in Isoton® II electrolyte (Coulter Corporation, Miami, Fla.) using a four-blade, 4.45 centimeter diameter propeller stirrer. It is expected that the sizes of the particles in the statistically large population of particles of amorphous precipitated silica of the present invention may be reduced during processing of the ingredients to prepare the dentifrice composition. Accordingly, the particle sizes of the statistically large population of particles of amorphous precipitated silica of the present invention present in the dentifrice composition may on the whole be smaller than those of the raw amorphous precipitated silica used to prepare the dentifrice composition.

Variations in the parameters and/or conditions during production result in variations in the types of precipitated silicas produced. Although they are all broadly precipitated silicas, the types of precipitated silicas often differ significantly in physical properties and sometimes in chemical properties. These differences in properties are important and often result in one type being especially useful for a particular purpose but of marginal utility for another purpose, whereas another type is quite useful for that other purpose but only marginally useful for the first purpose.

A method has been found for producing the statistically large population of particles of amorphous precipitates silica of the present invention. Accordingly, a second embodiment of the invention is a method for producing a statistically large population of particles of amorphous precipitated silica having a glassy phase fraction in the range of from 0.3 to 30 area percent, the process comprising: (a) establishing an initial aqueous alkali metal silicate solution containing from 0.48 to 1.05 moles $M_2O$ per liter and having an $SiO_2$:$M_2O$ molar ratio of from 2.0 to 3.7; (b) over a period of from 15 to 150 minutes and with agitation, adding acid to the initial aqueous alkali metal silicate solution at a temperature of from 80° C. to 99° C. to neutralize from 10 to 80 percent of the $M_2O$ present in the initial aqueous alkali metal solution and thereby to form a first reaction mixture; (c) aging the first reaction mixture with agitation at a temperature of from 80° C. to 99° C. for a period of from 10 to 90 minutes; (d) adding acid to the aged first reaction mixture with agitation at a temperature of from 80° C. to 99° C. to neutralize the $M_2O$ present and to form a second reaction mixture; (e) separating a statistically large population of particles of amorphous precipitated silica from most of the liquid of the second reaction mixture; (f) washing the separated statistically large population of particles of amorphous precipitated silica with water; and (g) drying the washed statistically large population of particles of amorphous precipitated silica, wherein: (h) the alkali metal silicate is lithium silicate, sodium silicate, potassium silicate, or a mixture thereof; and (i) M is lithium, sodium, potassium, or a mixture thereof.

The composition of the initial aqueous alkali metal silicate solution established in step (a) may vary widely. Generally the initial aqueous alkali metal silicate solution comprises from 0.48 to 1.05 moles $M_2O$ per liter. In many cases the initial aqueous alkali metal silicate solution comprises from 0.5 to 0.8 moles $M_2O$ per liter. From 0.55 to 0.73 moles $M_2O$ per liter is preferred. Usually the initial aqueous alkali metal silicate solution has an $SiO_2$:$M_2O$ molar ratio of from 2.5 to 3.7. Often the $SiO_2$:$M_2O$ molar ratio is from 3.0 to 3.5. Preferably the $SiO_2$:$M_2O$ molar ratio is from 3.1 to 3.3.

The acid used in the process may also vary widely. In general, the acid added in steps (b) and (d) should be strong enough to neutralize alkali metal silicate and cause precipitation of silica. The acid used in the various acid addition steps may be the same or different, but preferably it is the same. It is preferred to use strong acid throughout the method. Examples of the strong acids include sulfuric acid, hydrochloric acid, nitric acid, phosphoric acid, and acetic acid. The strong mineral acids such as sulfuric acid, hydrochloric acid, nitric acid, and phosphoric acid are preferred; sulfuric acid is especially preferred.

The acid addition of step (b) is made over a period of from 15 to 150 minutes. Frequently the acid addition of step (b) is made over a period of from 30 to 90 minutes. From 45 to 75 minutes is preferred.

The temperature of the reaction mixture during the acid addition of step (b) is in the range of from 75° C. to 99° C. In many instances the temperature is in the range of from 80° C. to 99° C. From 90° C. to 98° C. is preferred.

From 7 to 80 percent of the $M_2O$ present in the initial aqueous alkali metal silicate solution is neutralized during the acid addition of step (b). Often from 10 to 50 percent of the $M_2O$ present in the initial aqueous alkali metal silicate solution is neutralized during the acid addition of step (b). Preferably from 15 to 35 percent of the $M_2O$ is neutralized.

The temperature of the first reaction mixture during the aging of step (c) is in the range of from 75° C. to 99° C. Often the temperature is in the range of from 80° C. to 99° C. From 90° C. to 98° C. is preferred.

The aging in step (c) is for a period of from 5 to 120 minutes. In many cases the first reaction mixture is aged for a period of from 10 to 90 minutes. A period of from 30 to 60 minutes is preferred.

The acid addition of step (d) is preferably, but not necessarily, made at the same rate as the acid addition of step (b). Usually the acid addition of step (d) is made over a period of from 60 to 175 minutes. Often the acid addition is made over a period of from 90 to 165 minutes. From 120 to 150 minutes is preferred.

The temperature of the reaction mixture during the acid addition of step (d) is in the range of from 75° C. to 99° C. In many instances the temperature is in the range of from 80° C. to 99° C. From 90° C. to 98° C. is preferred.

The separation of step (e) may be accomplished by one or more techniques for separating solids from liquid such as, for example, filtration, centrifugation, decantation, and the like.

The washing of step (f) may be accomplished by any of the procedures known to the art for washing solids.

Examples of such procedures include passing water through a filter cake, and reslurring the statistically large population of particles of amorphous precipitated silica in water followed by separating the solids from the liquid. One washing cycle or a succession of washing cycles may be employed as desired. The primary purpose of washing is to remove salt formed by the various neutralizations to desirably low levels. Usually the statistically large population of particles of amorphous precipitated silica is washed until the concentration of salt in the dried statistically large population of particles of amorphous precipitated silica is less than or equal to 2 percent by weight. Often the statistically large population of particles of amorphous precipitated silica is washed until the concentration of salt is less than or equal to 1.5 percent by weight. Preferably the statistically large population of particles of amorphous precipitated silica is washed until the concentration of salt is less than or equal to one percent by weight.

The drying of step (g) may also be accomplished by one or more known techniques. Preferably the statistically large population of particles of amorphous precipitated silica is dispersed in water and spray dried in a column of hot air. The temperature at which drying is accomplished is not critical, but the usual practice is to employ temperatures of at least 70° C. Generally the drying temperature is less than 700° C. In most cases drying is continued until the statistically large population of particles of amorphous precipitated silica has the characteristics of a powder. Ordinarily the dried statistically large population of particles of amorphous precipitated silica is not absolutely anhydrous but contains bound water (from 2 to 5 weight percent) and adsorbed water (from 1 to 7 weight percent) in varying amounts, the latter depending partly upon the prevailing relative humidity. Adsorbed water is that water which is removed from the silica by heating at 105° C. for 24 hours at atmospheric pressure in a laboratory oven. Bound water is that water which is removed by additionally heating the silica at calcination temperatures, for example, from 1000° C. to 1200° C.

An optional step which may be employed is size reduction. Size reduction techniques are themselves well known and may be exemplified by milling. Examples of mills that may be used include ball mills, rod mills, hammer mills, and fluid energy mills. Fluid energy milling using air or superheated steam as the working fluid is very useful. Fluid energy mills are themselves well known. See, for example, *Perry's Chemical Engineers Handbook*, 4th Edition, McGraw-Hill Book Company, New York, (1963), Library of Congress Catalog Card Number 6113168, pages 8–42 and 8–43; McCabe and Smith, *Unit Operations of Chemical Engineering*, 3rd Edition, McGraw-Hill Book Company, New York (1976), ISBN 0-07-044825-6, pages 844 and 845; F. E Albus, "The Modern Fluid Energy Mill", *Chemical Engineering Progress*, Volume 60, No. 6 (June 1964), pages 102–106, the entire disclosures of which are incorporated herein by reference. In fluid energy mills the solid particles are suspended in a gas stream and conveyed at high velocity in a circular or elliptical path. Some reduction occurs when the particles strike or rub against the walls of the confining chamber, but most of the reduction is believed to be caused by interparticle attrition. Irrespective of the method employed, size reduction is usually conducted until the distribution of gross particle sizes is as described above in respect of the first embodiment of the invention.

The degrees of agitation used in the various steps of the method may vary considerably. The agitation employed during the addition of one or more reactants should be at least sufficient to provide a thorough dispersion of the reactants and reaction mixture so as to avoid more than trivial locally high concentrations of reactants and to ensure that silica deposition occurs substantially uniformly thereby avoiding gellation on the macro scale. The agitation employed during aging should be at least sufficient to avoid settling of solids to ensure that silica deposition occurs substantially uniformly throughout the mass of silica particles rather than preferentially on those particles at or near the top of a settled layer of particles. The degrees of agitation may, and preferably are, greater than these minimums. In general, vigorous agitation is preferred.

A preferred embodiment within the second embodiment of the invention is a method for producing a statistically large population of particles of amorphous precipitated silica having a glassy phase fraction in the range of from 1 to 30 area percent, the process comprising: (a) establishing an initial aqueous sodium silicate solution containing from 0.5 to 0.8 moles $Na_2O$ per liter and having an $SiO_2:Na_2O$ molar ratio of from 2.5 to 3.7; (b) over a period of from 30 to 90 minutes and with agitation, adding sulfuric acid to the initial aqueous sodium silicate solution at a temperature of from 90° C. to 98° C. to neutralize from 15 to 35 percent of the $Na_2O$ present in the initial aqueous sodium silicate solution and thereby to form a first reaction mixture; (c) aging the first reaction mixture with agitation at a temperature of from 90° C. to 98° C. for a period of from 30 to 60 minutes; (d) adding sulfuric acid to the aged first reaction mixture with agitation at a temperature of from 90° C. to 98° C. to neutralize the $Na_2O$ present and to form a second reaction mixture; (e) separating a statistically large population of particles of amorphous precipitated silica from most of the liquid of the second reaction mixture; (f) washing the separated statistically large population of particles of amorphous precipitated silica with water; and (g) spray drying the washed statistically large population of particles of amorphous precipitated silica.

It is understood that one or more ranges in the preferred embodiment may be used in lieu of the corresponding broader range or ranges in the broader second embodiment of the invention.

The statistically large populations of particles of amorphous precipitated silicas described above are especially effective as abrasives for dentifrice compositions. Accordingly, in a dentifrice composition containing a statistically large population of particles of amorphous precipitated silica abrasive, a third embodiment of the invention is the improvement wherein the statistically large population of particles of amorphous precipitated silica comprise pigmentary phase particles and glassy phase particles and have a glassy phase fraction in the range of from 1 to 30 area percent. The above discussion in respect of the statistically large population of particles of amorphous precipitated silica of the first embodiment of the invention, its properties, and its characteristics, is applicable to this embodiment.

Ordinarily the statistically large population of particles of amorphous precipitated silica abrasive of the present invention constitutes from 3 to 80 percent by weight of the dentifrice composition. Often the statistically large population of particles of amorphous precipitated silica abrasive constitutes from 4 to 35 percent by weight of the dentifrice composition. From 5 to 25 percent by weight is preferred. Other abrasive may optionally be present when desired.

The other ingredients in the dentifrice composition are conventional and are used in their customary amounts to accomplish their customary purposes.

The dentifrice composition may be a free-flowing powder, but preferably it is a toothpaste.

In most cases the toothpaste of the invention has a Radioactive Dentine Abrasion Test value (RDA) in the range of from 40 to 250. In many cases the RDA is in the range of from 60 to 200. From 70 to 150 is preferred. As used herein and in the claims the procedure for determining the RDA generally follows the method for assessment of dentifrice abrasivity recommended by the American Dental Association (ADA) as published in Grabenstetter et al., "The Measurement of the Abrasion of Human Teeth by Dentifrice Abrasives: A Test Utilizing Radioactive Teeth", *Journal of Dental Research*, 37 1060–1068 (1958). In procedure used herein, extracted human teeth are irradiated with a neutron flux and subjected to a standard brushing regime. The radioactive phosphorous 32 removed from the dentin in the roots is used as the index of the abrasion of the dentifrice tested. One thousand brush strokes are performed using a reference slurry containing 10 grams of a reference calcium pyrophosphate having an RDA value assigned by the ADA in 50 milliliters of 0.5% aqueous sodium carboxymethyl cellulose solution. One thousand brush strokes are also performed using a test slurry containing 25 grams of toothpaste in 50 milliliters of tap water. The RDA of the toothpaste is then determined according to the general procedure of the Grabenstetter et al., paper.

The invention is further described in conjunction with the following examples which are to be considered illustrative rather than limiting, and in which all parts are parts by weight and all percentages are percentages by weight unless otherwise specified.

STANDARD TOOTHPASTE PREPARATION

In Examples 1–3 which follow, a standard toothpaste was used for testing the abrasive silicas. The standard toothpaste was prepared as follows using the ingredients in the proportions shown in Table 1.

TABLE 1

| Ingredient Number | Ingredient | Proportions, parts by wt. |
|---|---|---|
| 1 | 70% Noncrystallizing Sorbitol | 49.66 |
| 2 | Glycerin | 10.0 |
| 3 | Polyethylene Glycol, Molecular Weight 600 | 3.0 |
| 4 | Sodium Benzoate | 0.5 |
| 5 | Sodium Fluoride | 0.24 |
| 6 | Hercules 7MXF Sodium Carboxymethylcellulose | 0.5 |
| 7 | Sodium Saccharin | 0.3 |
| 8 | Water | 10.0 |
| 9 | 1% Aqueous Food Color Solution | 0.1 |
| 10 | Abrasive Silica | 18.0 |
| 11 | W. R. Grace Sylox® 15 Silica Thickener | 5.5 |
| 12 | Sodium Lauryl Sulfate | 1.2 |
| 13 | Quest International Spearmint TP 1709 Flavor | 1.0 |

Ingredients 2 and 3 are mixed in a beaker for from 3 to 5 minutes with an impeller-type stirrer. Ingredients 4, 5, 6, and 7 are added to the mixture and stirred with an electric stirrer for 5 minutes. A premixed combination of Ingredients 5 and 6 is added and the mixture is stirred for 5 minutes. Ingredient 1 is added and the mixture is stirred for 5 minutes. Ingredient 9 is added and the mixture is stirred for 5 minutes. The resulting mixture is transferred from the beaker to a Ross mixer. While mixing for 15 minutes at a speed setting of 2, air is evacuated from the mixer. The vacuum is broken and Ingredient 10 is added. The mixer is resealed and deaerated for 2 minutes. The contents are mixed under vacuum at a speed setting of 1 until all powder is dispersed in the slurry. The vacuum is broken and Ingredient 11 is added. The mixer is resealed and deaerated for 2 minutes. The contents of the mixer are mixed under vacuum at a speed setting of 1 until all powder is dispersed in the slurry. The mixing speed is increased to a setting of 4 and the mixture is mixed under vacuum for 10 minutes. The vacuum is broken and Ingredient 13 is added. The contents of the mixer are mixed without vacuum at a speed setting of 1 for 1 minute. Ingredient 12 is added. The mixer is resealed and deaerated for 5 minutes. The contents of the mixer are mixed under vacuum at a speed setting of 1 until all powder is dispersed. The mixing speed is increased to a setting of 4 and the mixture is mixed under vacuum at that speed for 10 minutes. the vacuum is broken and the resulting toothpaste is transferred to toothpaste tubes.

EXAMPLE 1

A 100-liter reactor equipped with two agitators was charged with 50 liters of aqueous sodium silicate solution containing 0.645 moles of $Na_2O$ per liter and having an $SiO_2:Na_2O$ molar ratio of 3.29. Over a period of 30 minutes while the larger low speed agitator was run at 250 revolutions per minute (rpm) and the smaller high speed agitator was run at 2000 rpm, and while the temperature of the reaction mixture was maintained at 98° C., sufficient 96% sulfuric acid was added to neutralize one-sixth of the $Na_2O$ initially present to thereby form a first reaction mixture. The acid was added near the high speed agitator to insure rapid distribution of the acid throughout the reaction mixture. For the next 90 minutes the first reaction mixture was aged at 98° C. with the low speed agitator running and the high speed agitator shut off. The high speed agitator was then turned on and 96% sulfuric acid was added over a period of 150 minutes to form a second reaction mixture which had a final pH of 4.0. Four ten-liter portions of the of the second reaction mixture were each filtered on a separate 32 centimeter Buchner funnel. Each filter cake was washed three times with 2 liter of fresh water. The four washed filter cakes were combined and liquefied using a 5-centimeter high shear stainless steel Cowles blade. The resulting liquefied mixture was diluted with water to 25 percent by weight solids and then spray dried. The dried solids were milled to provide an amorphous precipitated silica product. Results of testing the product are shown in Table 2.

TABLE 2

| | |
|---|---|
| Glassy Phase Fraction, area % | 2.34 |
| Surface Area, $m^2/g$ | 104 |
| DBP Oil Absorption, $cm^3/100$ g | 112 |
| Particle Size Distribution, μm | |
| $D_{10}$ | 20.0 |
| $D_{50}$ | 10.9 |
| $D_{90}$ | 3.3 |

Standard toothpaste was formulated using the amorphous precipitated silica product as the abrasive silica. The RDA of the toothpaste was 86.

FIG. 1 is a photomicrograph showing images of the amorphous precipitated silica product of this Example 1 dispersed in an oil having an index of refraction, $n_D^{25}$, of 1.550±0.0002. The photomicrograph was originally captured as a digital color image at 1200× using a video recording system. The image was then transferred to an image analysis computer and thereafter converted to a gray level image. The photomicrograph contains images 1 of glassy phase particles, some of which have ribs 2. It also contains images 3 of pigmentary particles.

Figure 2:
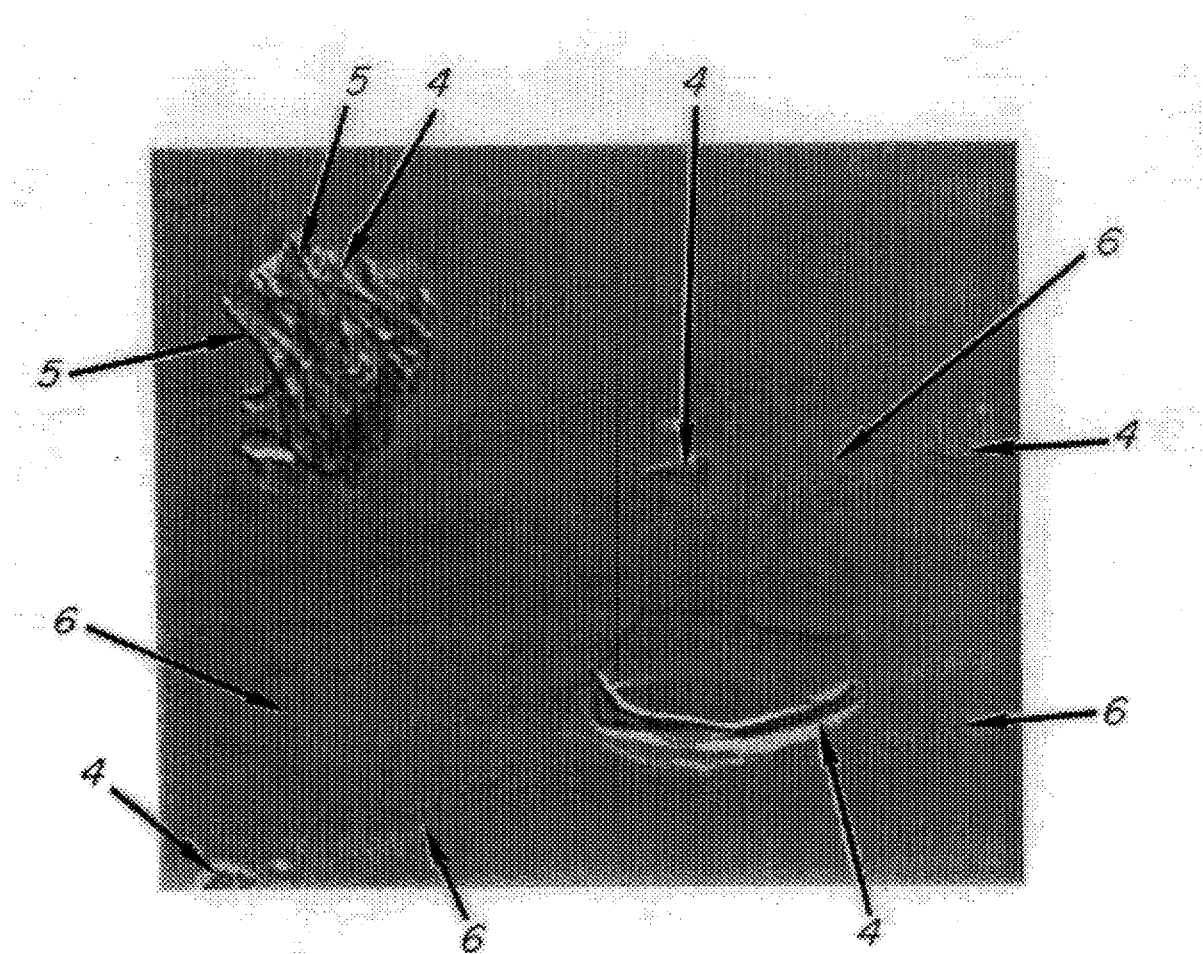

FIG. 2 is a photomicrograph showing images of the amorphous precipitated silica product of this Example 1 dispersed in matching index immersion oil. The photomicrograph was originally captured as a digital color image at 1200× using a video recording system. The image was then transferred to an image analysis computer and thereafter converted to a gray level image. The photomicrograph contains images 4 of glassy phase particles, some of which have wrinkles 5. It also contains vestiges 6 of images of pigmentary particles. The vestiges are faintly visible because it is not possible to completely match the indices of refraction of the immersion oil and the pigmentary particles for all visible wavelengths of light (the Christiansen effect).

EXAMPLE 2

A reactor larger than that of Example 1 was equipped with two agitators. Aqueous sodium silicate solution containing 0.645 moles of $Na_2O$ per liter and having an $SiO_2:Na_2O$ molar ratio of 3.33 was added until the reactor was two-thirds full by volume. Over a period of 120 minutes while the first agitator was run at low speed and the second agitator was run at high speed and while the temperature of the reaction mixture was maintained at 95° C.±0.2, sufficient 22% sulfuric acid was added to neutralize two-thirds of the $Na_2O$ initially present to thereby form a first reaction mixture. The acid was added near the high speed agitator to insure rapid distribution of the acid throughout the reaction mixture. For the next 90 minutes the first reaction mixture was aged at 95° C. with the first agitator running and the second agitator shut off. The second agitator was then turned on and 22% sulfuric acid was added over a period of 60 minutes to form a second reaction mixture which had a final pH of 4.0. The second reaction mixture was filtered and washed with fresh water on a filter press. The washed filter cake was liquefied by stirring, diluted with water to about 27% percent by weight solids and then spray dried. The dried solids were milled to provide an amorphous precipitated silica product. Results of testing the product are shown in Table 3.

TABLE 3

| | |
|---|---|
| Glassy Phase Fraction, area % | 3.76 |
| Surface Area, m²/g | 75 |
| DBP Oil Absorption, cm³/100 g | 90 |
| Particle Size Distribution, μm | |
| $D_{10}$ | 16. 5 |
| $D_{50}$ | 8.9 |
| $D_{90}$ | 2.8 |

Standard toothpaste was formulated using the amorphous precipitated silica product as the abrasive silica. The RDA of the toothpaste was 190.

EXAMPLE 3 (Comparative)

Two commercially available amorphous silicas (Commercial Silica A and Commercial Silica B, respectively) were also tested. In determining the glassy phase fraction of Commercial Silica A, the procedure deviated from that described above only in that the samples transferred to the tin cups each weighed 0.500±0.029 milligram. The glassy phase fraction of Commercial Silica B was determined without such deviation. Results of the testing are shown in Table 4.

TABLE 4

| Commercial Silica | A | B |
|---|---|---|
| Glassy Phase Fraction, area % | 0.08 | 0.11 |
| Surface Area, m²/g | 97 | 208 |
| DBP Oil Absorption, cm³/100 g | 91 | 113 |
| Particle Size Distribution, μm | | |
| $D_{phd}$ 10 | 24.6 | 24.5 |
| $D_{50}$ | 10.6 | 11.7 |
| $D_{90}$ | 3.6 | 3.6 |

Standard toothpaste was formulated using Commercial Silica A as the abrasive silica. The RDA of the toothpaste was 82.

Standard toothpaste was also formulated using Commercial Silica B as the abrasive silica. The RDA of the toothpaste was 102.

EXAMPLE 4 (Comparative)

A third commercially available amorphous silica (Commercial Silica C) was also tested. Results of the testing are shown in Table 5.

TABLE 5

| | |
|---|---|
| Glassy Phase Fraction, area % | 42.66 |
| Surface Area, m²/g | 809 |
| DBP Oil Absorption, cm³/100 g | 123 |
| Particle Size Distribution, μm | |
| $D_{10}$ | 12.9 |
| $D_{50}$ | 7.0 |
| $D_{90}$ | 2.6 |

A toothpaste was prepared according to the general procedure described in respect of the standard toothpaste but using the ingredients in the proportions shown in Table 6.

TABLE 6

| Ingredient Number | Ingredient | Proportions, parts by wt. |
|---|---|---|
| 1 | 70% Noncrystallizing Sorbitol | 41.31 |
| 2 | Glycerin | 25.0 |
| 3 | Polyethylene Glycol, Molecular Weight 600 | 3.0 |
| 4 | Sodium Benzoate | 0.5 |
| 5 | Sodium Monofluorophosphate | 0.76 |
| 6 | Hercules 7MXF Sodium Carboxymethylcellulose | 0.35 |
| 7 | Sodium Saccharin | 0.3 |
| 8 | Water | 3.0 |
| 9 | 1% Aqueous Food Color Solution | 0.07 |
| 10 | Commercial Silica C | 18.0 |
| 11 | W. R. Grace Sylodent ® 15 Silica Thickener | 5.5 |
| 12 | Sodium Lauryl Sulfate | 1.2 |
| 13 | Quest International Spearmint TP 1709 Flavor | 1.0 |

The RDA of the toothpaste was 92.

Although the present invention has been described with reference to specific details of certain embodiments thereof, it is not intended that such details should be regarded as limitations upon the scope of the invention except insofar as they are included in the accompanying claims.

We claim:

1. A statistically large population of particles of amorphous precipitated silica comprising pigmentary phase particles and glassy phase particles and having a glassy phase fraction in the range of from 0.3 to 30 area percent.

2. The statistically large population of particles of amorphous precipitated silica of claim 1 having:
   (a) a surface area in the range of from 30 to 400 m²/g; and
   (b) a DBP oil absorption in the range of from 60 to 200 cm³/100 g.

3. The statistically large population of particles of amorphous precipitated silica of claim 1 wherein the median particle size by volume of said statistically large population of particles of amorphous precipitated silica is in the range of from 2 to 50 μm.

4. The statistically large population of particles of amorphous precipitated silica of claim 3 wherein:
   (a) at least 90 percent by volume of said statistically large population of particles of amorphous precipitated silica has particle sizes less than 100 μm; and
   (b) at least 90 percent by volume of said statistically large population of particles of amorphous precipitated silica has particle sizes greater than 0.5 μm.

5. The statistically large population of particles of amorphous precipitated silica of claim 1 wherein the median particle size by volume of said statistically large population of particles of amorphous precipitated silica is in the range of from 2 to 20 μm.

6. The statistically large population of particles of amorphous precipitated silica of claim 5 wherein:
   (a) at least 90 percent by volume of said statistically large population of particles of amorphous precipitated silica has particle sizes less than 50 μm; and
   (b) at least 90 percent by volume of said statistically large population of particles of amorphous precipitated silica has particle sizes greater than 0.5 μm.

7. The statistically large population of particles of amorphous precipitated silica of claim 1 having a glassy phase fraction in the range of from 0.4 to 10 area percent.

8. The statistically large population of particles of amorphous precipitated silica of claim 1 having a glassy phase fraction in the range of from 0.5 to 5 area percent.

9. The statistically large population of particles of amorphous precipitated silica of claim 1 wherein at least some of said glassy phase particles exhibit one or more morphologies selected from:
   (a) moderately thick tablets having ribs and/or wrinkles;
   (b) rounded equant nuggets; and
   (c) thin brittle films.

10. A dentifrice composition comprising the statistically large population of particles of amorphous precipitated silica of claim 1.

11. The dentifrice composition of claim 10 where in said statistically large population of particles of amorphous precipitated silica constitutes from 3 to 80 percent by weight of said dentifrice composition.

12. The dentifrice composition of claim 11 which is toothpaste.

13. The dentifrice composition of claim 12 wherein said toothpaste has an RDA in the range of from 40 to 250.

14. A dentifrice composition comprising the statistically large population of particles of amorphous precipitated silica of claim 7.

15. The dentifrice composition of claim 14 wherein said statistically large population of particles of amorphous precipitated silica constitutes from 3 to 80 percent by weight of said dentifrice composition.

16. The dentifrice composition of claim 15 which is toothpaste.

17. The dentifrice composition of claim 16 wherein said toothpaste has an RDA in the range of from 40 to 250.

18. A dentifrice composition comprising the statistically large population of particles of amorphous precipitated silica of claim 8.

19. The dentifrice composition of claim 18 where in said statistically large population of particles of amorphous precipitated silica constitutes from 3 to 80 percent by weight of said dentifrice composition.

20. The dentifrice composition of claim 19 which is toothpaste.

21. The dentifrice composition of claim 20 wherein said toothpaste has an RDA in the range of from 40 to 250.

22. A method for producing a statistically large population of particles of amorphous precipitated silica having a glassy phase fraction in the range of from 0.3 to 30 area percent, said process comprising:
   (a) establishing an initial aqueous alkali metal silicate solution containing from 0.48 to 1.05 moles $M_2O$ per liter and having an $SiO_2:M_2O$ molar ratio of from 2.0 to 3.7;
   (b) over a period of from 15 to 150 minutes and with agitation, adding acid to said initial aqueous alkali metal silicate solution at a temperature of from 80° C. to 99° C. to neutralize from 10 to 80 percent of the $M_2O$ present in said initial aqueous alkali metal solution and thereby to form a first reaction mixture;
   (c) aging said first reaction mixture with agitation at a temperature of from 80° C. to 99° C. for a period of from 10 to 90 minutes;
   (d) adding acid to the aged first reaction mixture with agitation at a temperature of from 80° C. to 99° C. to neutralize the $M_2O$ present and to form a second reaction mixture;
   (e) separating a statistically large population of particles of amorphous precipitated silica from most of the liquid of said second reaction mixture;
   (f) washing the separated statistically large population of particles of amorphous precipitated silica with water; and
   (g) drying the washed statistically large population of particles of amorphous precipitated silica,
wherein:
   (h) said alkali metal silicate is lithium silicate, sodium silicate, potassium silicate, or a mixture thereof; and
   (i) M is lithium, sodium, potassium, or a mixture thereof.

23. The method of claim 22 wherein said dried statistically large population of particles of amorphous precipitated silica is milled.

24. The method of claim 22 wherein:
   (a) said initial aqueous alkali metal silicate solution is aqueous sodium silicate solution containing from 0.5 to 0.8 moles $Na_2O$ per liter and having an $SiO_2:Na_2O$ molar ratio of from 2.5 to 3.7;
   (b) sulfuric acid is added over a period of from 30 to 90 minutes with agitation to said initial aqueous sodium silicate solution at a temperature of from 90° C. to 98° C. to neutralize from 15 to 35 percent of the $Na_2O$ present in said initial aqueous sodium silicate solution and thereby to form said first reaction mixture;
   (c) said first reaction mixture is aged with agitation at a temperature of from 90° C. to 98° C. for a period of from 30 to 60 minutes; and
   (d) sulfuric acid is added to said aged first reaction mixture with agitation at a temperature of from 90° C. to 98° C. to neutralize the $Na_2O$ present and to form said second reaction mixture.

* * * * *